US 8,827,317 B2

(12) United States Patent
Karla et al.

(10) Patent No.: US 8,827,317 B2
(45) Date of Patent: Sep. 9, 2014

(54) MEDICAL DEVICE ADAPTOR

(75) Inventors: Sean R. Karla, Syracuse, NY (US); Raymond A. Lia, Auburn, NY (US); Jamie H. Bartenstein, East Syracuse, NY (US); Robert L. Vivenzio, Auburn, NY (US); Victor G. Ianno, Seldwinsville, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 1030 days.

(21) Appl. No.: 12/776,019

(22) Filed: May 7, 2010

(65) Prior Publication Data

US 2011/0275945 A1 Nov. 10, 2011

(51) Int. Cl.
*F16L 39/00* (2006.01)
*A61M 39/10* (2006.01)

(52) U.S. Cl.
CPC .............. *A61M 39/10* (2013.01); *A61M 39/105* (2013.01); *A61M 2039/1022* (2013.01); *A61M 2039/1077* (2013.01); *Y10S 285/921* (2013.01)
USPC ......... 285/124.1; 285/179; 285/319; 285/921

(58) Field of Classification Search
CPC ..................... A61M 39/10; A61M 2039/1022; A61M 2039/1077; A61M 39/105
USPC .............. 285/133.21, 179, 182, 125.1, 145.2, 285/148.4, 184, 190, 278, 280, 281, 285/124.1–124.5, 25, 26, 345, 319, 921, 285/121.3; 210/443, 232; D23/263, 264; 239/290; 138/89.1–90; 215/309, 215/273–277, 280–282, 290, 341, 349, 215/350; 137/594; 604/533–539, 284; 277/317, 321, 372, 373, 397, 598, 608, 277/609, 615, 616, 625, 630, 637
See application file for complete search history.

(56) References Cited

U.S. PATENT DOCUMENTS

| 3,770,205 | A | * | 11/1973 | Proctor et al. ................. 239/317 |
| 5,597,021 | A | * | 1/1997 | Crossdale et al. ............ 141/346 |
| 5,837,137 | A | * | 11/1998 | Janik ............................. 210/232 |
| 6,578,428 | B1 | | 6/2003 | Dromms et al. |
| 6,746,406 | B2 | | 6/2004 | Lia et al. |
| 6,796,186 | B2 | | 9/2004 | Lia et al. |
| D575,871 | S | | 8/2008 | Wawro et al. |
| 7,647,111 | B2 | | 1/2010 | Ries et al. |

(Continued)

FOREIGN PATENT DOCUMENTS

EP 2161051 A1 3/2010

OTHER PUBLICATIONS

2003 Association for the Advancement of Medical Instrumentation (ANSI/AAMI SP 10:2002) 1 page, date: May 14, 2010.

(Continued)

*Primary Examiner* — James Hewitt
*Assistant Examiner* — Jay R Ripley

(57) ABSTRACT

A medical device adaptor includes a housing defining a mounting port and a circumscribing outer wall, a fluid passage extending substantially through the adaptor to the mounting port, and a pair of mounting shoulders spaced circumferentially along the outer wall. The pair of mounting shoulders extend transverse from the outer wall. The medical device adaptor also includes an insert disposed within the mounting port. The insert defines a thru hole at least partially aligned with the fluid passage.

18 Claims, 8 Drawing Sheets

(56) References Cited

U.S. PATENT DOCUMENTS

| | | |
|---|---|---|
| 7,670,296 B2 | 3/2010 | Molnar et al. |
| 2004/0019286 A1 | 1/2004 | Lia et al. |
| 2005/0222634 A1 | 10/2005 | Flickinger et al. |
| 2006/0217618 A1 | 9/2006 | Lia et al. |
| 2006/0293600 A1 | 12/2006 | Wawro et al. |
| 2009/0008318 A1* | 1/2009 | Anes et al. .................. 210/262 |
| 2009/0048638 A1 | 2/2009 | Rey et al. |
| 2009/0318818 A1 | 12/2009 | Whitaker et al. |

OTHER PUBLICATIONS

International Search Report and Written Opinion for PCT/US2011/034759, Dated Feb. 8, 2012 (12 pages).

* cited by examiner

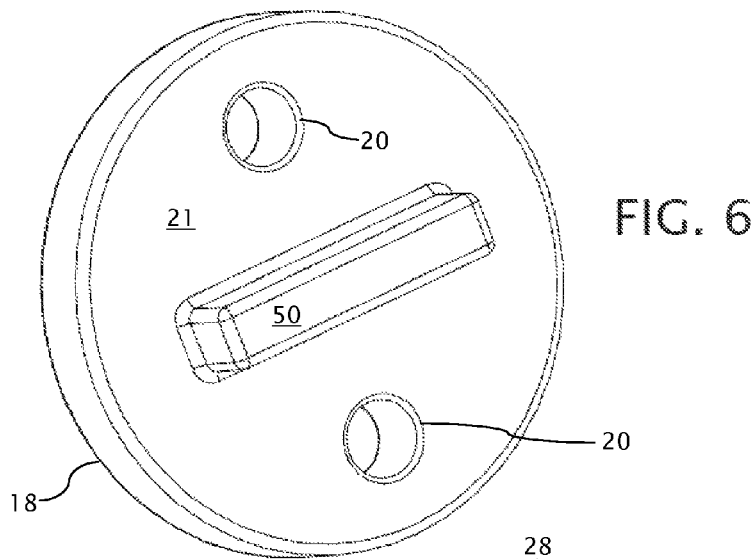
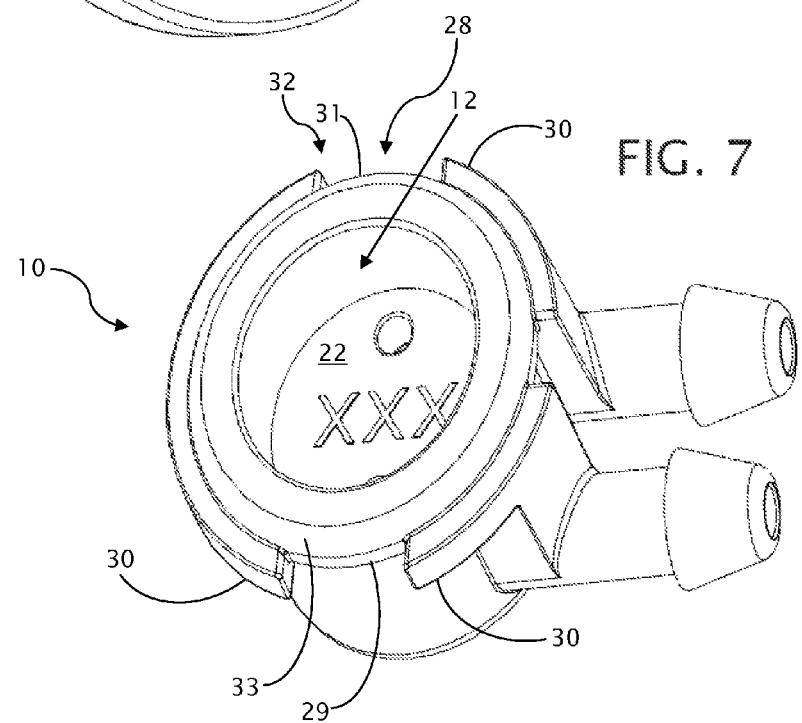

MEDICAL DEVICE ADAPTOR

CROSS-REFERENCE TO RELATED APPLICATIONS

None.

STATEMENT REGARDING FEDERALLY SPONSORED RESEARCH OR DEVELOPMENT

Not applicable.

REFERENCE TO A "SEQUENCE LISTING"

Not applicable.

BACKGROUND OF THE INVENTION

1. Field of the Invention

The present disclosure generally relates to an adaptor for use in connecting medical devices and, in particular, to a universal adaptor configured to connect traditional medical devices to monitors or other medical instruments equipped with standardized fittings.

2. Description of Related Art

Healthcare facilities such as hospitals, emergency rooms, trauma centers, physician's offices, and the like commonly employ a wide array of different medical devices for patient care. Such known medical devices include, for example, sphygmomanometers or other instruments for measuring blood pressure, stethoscopes or other acoustic medical instruments for listening to internal bodily sounds, and heart monitors or electrocardiographic devices used to analyze the activities of the heart. Due to the wide variety of medical devices used in modern healthcare, it is desirable for healthcare facilities to standardize the connectability of such devices, to the extent possible.

For example, patients visiting such healthcare facilities may receive treatment in one or more different locations within the healthcare facility during a single visit. During such a visit, a first medical device, such as an inflatable blood pressure cuff, may be affixed to a patient at a first examining location. A physician at the first location may then measure the patient's blood pressure by connecting the blood pressure cuff to a blood pressure monitor located at the first treatment location, and this monitor may be equipped with a standardized fitting configured to mate with a corresponding standardized port of the blood pressure cuff. It is common for the patient to then be transferred to a second treatment location within the healthcare facility for further evaluation or care. To reduce set-up time at this second location, it may be convenient for the physician at the first location to leave, for example, the blood pressure cuff, and/or other medical devices connected to the patient for use at the second location. It follows that equipping the monitors and other instruments used at the second treatment location with the standardized fittings used at the first location would enable healthcare professionals to quickly and conveniently connect the blood pressure cuff and other like diagnostic equipment to the instruments at the second location upon the patient's arrival.

The standardization of connection fittings within healthcare facilities is already underway at some facilities, and standardized monitor or instrument fittings for use in connecting multiple different medical devices are known in the art. An example of such a standardized fitting is shown in, for example, U.S. Pat. No. D575,871S, assigned to Welch Allyn, Inc. of Skaneateles Falls, N.Y. Equipping, for example, blood pressure monitors, and/or other common medical devices with such a standardized fitting, and equipping blood pressure cuffs or other like diagnostic equipment with a corresponding connection port may streamline the process of examining and treating patients at multiple locations throughout the healthcare facility.

However, once a healthcare facility has standardized the fittings employed by each of the monitors, sensors, instruments, and/or other medical devices used in each of its treatment locations, the healthcare facility may still have a need for a universal component enabling healthcare professionals to quickly connect such standardized fittings to blood pressure cuffs and/or other diagnostic equipment having ports or other connections that do not mate with the standardized fittings being used. For example, if a patient is fitted with a blood pressure cuff or other diagnostic equipment employing a port that is not compatible with the standardized fittings used throughout the healthcare facility, the equipment would have to be removed from the patient, and the patient would have to be refitted with a compatible blood pressure cuff or other equipment before the patient could be evaluated and treated using the standardized blood pressure monitors and/or other medical devices. Refitting a patient in this way can be time consuming and may be uncomfortable for the patient depending upon the diagnostic equipment being employed. Moreover, such delay could possibly result in harm to the patient depending upon the patient's condition.

The embodiments of the present disclosure are aimed at overcoming one or more of the difficulties described above.

SUMMARY OF THE INVENTION

In an exemplary embodiment of the present disclosure, a medical device adaptor includes a housing defining a mounting port and a circumscribing outer wall, a fluid passage extending substantially through the adaptor to the mounting port, and a pair of mounting shoulders spaced circumferentially along the outer wall. The pair of mounting shoulders extend transverse from the outer wall. The medical device adaptor also includes an insert disposed within the mounting port. The insert defines a thru hole at least partially aligned with the fluid passage.

In such an exemplary embodiment, the insert defines a substantially planar sealing surface proximate the thru hole. The medical device adaptor defines a central axis, a first portion of the fluid passage extends substantially transverse to the central axis, and a second portion of the fluid passage extends substantially parallel to the central axis. The medical device adaptor further includes a connection stem extending transverse from the outer wall of the adaptor, and at least a portion of the fluid passage extends through the connection stem.

In another exemplary embodiment of the present disclosure, a medical device adaptor removably attachable to a standardized fitting includes a housing, and the housing defines a plurality of individual fluid passages extending therethrough. The adaptor also includes a plurality of connection stems, each connection stem corresponding to a respective one of the plurality of individual fluid passages, and a mounting port fluidly connected to the plurality of individual fluid passages. In such an exemplary embodiment, the adaptor also includes an insert disposed within the mounting port. The insert defines a plurality of thru holes, each thru hole being fluidly connected to a respective one of the plurality of individual fluid passages.

In such an exemplary embodiment, the medical device adaptor further includes a mounting shoulder disposed along an outer circumference of the housing. In addition, the medical device adaptor includes a flange extending along the outer circumference and the mounting shoulder is disposed at a gap in the flange.

In such an exemplary embodiment, the medical device adaptor further includes a flange extending along an outer circumference of the housing, the flange defines the first and second gaps, and the first and second gaps are disposed approximately 180 degrees apart. The medical device adaptor further includes a first mounting shoulder disposed at the first gap and a second mounting shoulder disposed at the second gap, and the flange further defines a third gap separating two of the plurality of connection stems.

In such an exemplary embodiment, the housing further defines a keyway disposed between two fluid passages of the plurality of individual fluid passages, and the insert defines a key disposed within the keyway, the key orienting the insert relative to the housing. In addition, each connection stem defines a portion of the respective one of the plurality of individual fluid passages. In such an exemplary embodiment, each connection stem defines a longitudinal axis and each fluid passage of the plurality of individual fluid passages extends along a respective one of the longitudinal axes. Moreover, a portion of each fluid passage of the plurality of individual fluid passages extends perpendicular to the respective one of the longitudinal axes, each thru hole of the plurality of thru holes extends perpendicular to the longitudinal axes, and the insert defines a sealing surface having a greater elasticity than the housing.

In another exemplary embodiment of the present disclosure, a medical device adaptor removably attachable to a standardized fitting includes a housing having a mounting port, the mounting port defined by a ceiling and a wall extending from the ceiling, and a pair of connection stems, each of the connection stems defining a respective fluid passage extending therethrough from respective orifices in the ceiling. the adaptor also includes an insert disposed adjacent to the ceiling, the insert defines a pair of thru holes, and each thru hole overlays a respective one of the orifices in the ceiling.

In such an exemplary embodiment, the ceiling further defines a keyway, and the insert defines a key disposed within the keyway. The adaptor also includes a pair of mounting shoulders disposed substantially opposite each other along an outer circumference of the housing.

In a further exemplary embodiment, a method of passing a signal between a first medical device and a second medical device includes providing an adaptor fluidly connected to the first medical device. The adaptor includes a mounting port, a fluid passage extending substantially through the adaptor to the mounting port, and an insert disposed within the mounting port. The adaptor also includes a pair of mounting shoulders spaced circumferentially along an outer wall of the adaptor, the pair of mounting shoulders extending transverse from the outer wall. Such an exemplary method also includes providing a fitting fluidly connected to the second medical device. The fitting includes a stem, and the stem defines an orifice and a sealing face surrounding the orifice. The fitting also includes a fluid passage extending substantially through the fitting to the orifice, and a pair of attachment legs extending proximate the stem. The exemplary method further includes inserting the stem into the mounting port, the pair of mounting shoulders governing orientation of the pair of attachment legs during the insertion, and forming a substantially fluid-tight seal between the sealing face and the insert.

In such an exemplary embodiment, the method also includes fluidly connecting the fluid passage of the adaptor and the fluid passage of the fitting, and inserting the stem comprises sliding the pair of attachment legs along the pair of mounting shoulders. In addition, the signal includes one of a sound signal and a pressure signal, and the first medical device includes one of a stethoscope and a blood pressure cuff. Such an exemplary method also includes passing the signal through a thru hole of the insert, and forming the substantially fluid-tight seal includes deforming a portion of the insert with the sealing face.

In yet another exemplary embodiment of the present disclosure, a method of forming a fluid connection between a first medical device and second medical device includes fluidly connecting an adaptor to the first medical device. In such an embodiment, the adaptor includes a mounting port, a fluid passage extending substantially through the adaptor to the mounting port, and a pair of a mounting shoulders extending laterally from an outer wall of the adaptor. The exemplary method also includes providing a first standardized fitting fluidly connected to the second medical device. In such an embodiment, the first standardized fitting includes a stem defining an orifice, a fluid passage extending substantially through the fitting to the orifice, and a pair of attachment legs extending proximate the stem. Such an exemplary method further includes engaging the pair of mounting shoulders with the attachment legs, the pair of mounting shoulders orienting the fitting relative to the adaptor. Such an exemplary method further includes positioning the stem within the mounting port, thereby forming a substantially fluid-tight seal between the adaptor and the first standardized fitting at the orifice, and fluidly connecting the fluid passage of the adaptor with the fluid passage of the first standardized fitting.

Such an exemplary method further includes disengaging the pair of mounting shoulders from the attachment legs, removing the stem from the mounting port, and fluidly connecting the fluid passage of the adaptor with a fluid passage of a second standardized fitting, wherein the second standardized fitting is substantially structurally similar to the first standardized fitting. In such an exemplary method, the second standardized fitting is connected to a third medical device, and the first standardized fitting is disposed in a first location in a healthcare facility, and the second standardized fitting is disposed in a second location in the healthcare facility different than the first location.

In another exemplary embodiment of the present disclosure, a medical device adaptor includes a mounting port, a fluid passage extending substantially through the adaptor to the mounting port, and a pair of a mounting shoulders extending transverse from an outer wall of the adaptor. In such an exemplary embodiment the mounting shoulders are disposed within separate gaps of a flange surrounding a portion of the outer wall.

In yet another exemplary embodiment of the present disclosure, a medical device adaptor is removably connectable to a standardized fitting. The adaptor includes a mounting shoulder configured to mate with an attachment leg of the fitting. The adaptor further includes a fluid passage extending substantially through the adaptor and configured for fluid connection with the fitting, and a sealing surface configured to form a substantially fluid-tight seal with a corresponding surface of the fitting.

In such an exemplary embodiment, the fitting defines a fluid passage, the fluid passage of the fitting being fluidly connected to the fluid passage of the adaptor upon connecting the fitting to the adaptor. In an additional exemplary embodiment, the adaptor defines a plurality of individual fluid passages extending substantially therethrough and the fitting defines a corresponding plurality of individual fluid passages. Each one of the individual fitting fluid passages being fluidly connected to a respective one of the individual adaptor fluid passages upon connecting the fitting to the adaptor. In another exemplary embodiment, the mounting shoulder orients the fitting relative to the adaptor upon connecting the fitting to the adaptor.

BRIEF DESCRIPTION OF THE SEVERAL VIEWS OF THE DRAWING

FIG. 6 is isometric view of an insert according to an exemplary embodiment of the present disclosure.

FIG. 7 is an isometric view of an exemplary medical device adaptor.

DETAILED DESCRIPTION OF THE DRAWINGS

Figure 1:
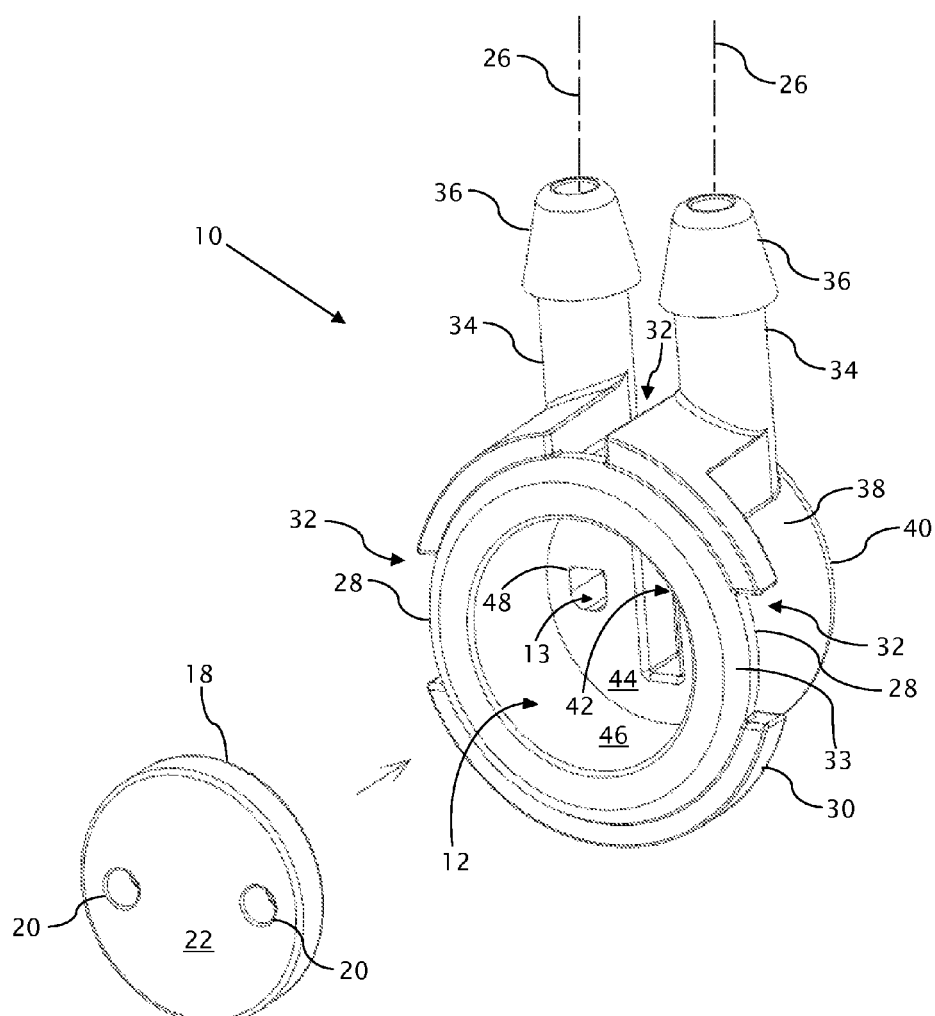
FIG. 1 is an exploded view of a medical device adaptor according to an exemplary embodiment of the present disclosure.

FIG. 1 illustrates a medical device adaptor 10 according to an exemplary embodiment of the present disclosure. Such an adaptor 10 may include, for example, a housing 40, and an insert 18 disposed within, mounted on, and/or otherwise connected to the housing 40. In additional exemplary embodiments, the insert 18 may be omitted, and the functions of the insert 18 may be performed by one or more components of the adaptor 10 described herein. For the duration of this disclosure, exemplary embodiments of the adaptor 10 including both the housing 40 and the insert 18 shall be described in greater detail unless otherwise specified.

The housing 40 may be made from any plastic, polymer, metal, alloy, and/or other like material known in the medical device arts. The material selected for the housing 40 may be medically approved and/or otherwise approved for use in healthcare applications. Such materials may be, for example, resistant to solvents and/or other chemicals commonly used in cleaning and sterilization. In addition, such materials may be at least partially resistant to the spread of germs, disease, viruses, and the like. Thus, such materials may assist in minimizing the problem of cross-contamination commonly seen in hospitals and other healthcare facilities.

The insert 18 may be made from any of the materials discussed above with regard to the housing 40, and the insert 18 may be made from a different material than the housing 40 in some exemplary embodiments. In addition, at least a portion of the insert 18 may be more malleable and/or elastic than the housing 40. For example, one or more surfaces of the insert 18 may be made from a different and relatively more elastic material than the material utilized in forming the housing 40.

The housing 40 and/or the insert 18 may be made from any process known in the art such as, for example, blow molding, thermoforming, or other known molding, machining, or material forming processes. It is understood that the process utilized to form the adaptor 10 and/or the insert 18 may depend on, for example, the materials used to form these components.

In an exemplary embodiment, the adaptor 10 may include at least one mounting port 12, one or more fluid passages 13 fluidly connected to the mounting port 12, and a pair of mounting shoulders 28. In addition, as shown in FIG. 1, an exemplary adaptor 10 may include one or more connection stems 34 extending from the housing 40, and the housing 40 may define a flange 30 extending along at least a portion of an outer circumference of the housing 40 and/or an outer wall 38 of the adaptor 10.

The mounting port 12 may have any shape, size, and/or other configuration convenient for accepting and/or otherwise mating with at least a portion of a medical device fitting. Exemplary fittings configured to mate with the mounting port 12 of the adaptor 10 are illustrated in FIGS. 8 through 11, and are further illustrated schematically in FIG. 12. Accordingly, such fittings shall be described in greater detail below. Although the mounting port 12 is illustrated as a substantially cylindrical channel or passage of the housing 40, it is understood that the mounting port 12 may be shaped, sized, and/or otherwise configured as desired to facilitate connection to such exemplary fittings. For example, the mounting port 12 may be substantially rectangular, substantially square, substantially D-shaped, substantially triangular, and/or any other shape to facilitate relatively easy connection thereto and sealability therewith.

In an exemplary embodiment, the mounting port 12 may be defined by a ceiling 44 and an inner wall 46 of the housing 40. In such an exemplary embodiment, the wall 46 may be substantially cylindrical, and the wall 46 may extend from the ceiling 44 at any desired angle. The ceiling 44 may be substantially planar, and to assist in effecting a substantially fluid-tight seal with components disposed within the mounting port 12, the ceiling 44 may be disposed substantially perpendicular to the wall 46. It is understood, however, that additional orientations of the ceiling 44 relative to the wall 46 may be desirable depending upon, for example, the configuration of the fitting with which the adaptor 10 is employed.

The ceiling 44 may define at least one orifice 48. In an exemplary embodiment, the ceiling 44 may define a plurality of orifices 48, and each orifice 48 correspond to a respective fluid passage 13 and/or connection stem 34 of the adaptor 10. The orifices 48 may have any shape, size, and/or configuration known in the art. The orifices 48 may facilitate the fluid connection of the fluid passages 13 with, for example the mounting port 12. In addition, when the insert 18 is disposed within the mounting port 12, the orifices 48 may facilitate a fluid connection between the fluid passages 13 of the adaptor 10 and thru holes 20 of the insert 18. In an exemplary embodiment, the orifices 48 may have a radius, diameter, circumference, and/or other dimension that is smaller than a corresponding dimension of the thru holes 20. In such an exemplary embodiment, a fluid such as air or water may pass from the orifices 48 to the thru holes 20 substantially unimpeded. In addition, in such an exemplary embodiment, such relative dimensions between the orifices 48 and the thru holes 20 may allow for slight misalignment of the insert 18 within the mounting port 12 during use with minimal effect on adaptor performance. In an exemplary embodiment, the orifices 48 may form at least a portion of the respective fluid passages 13 defined by the adaptor 10, and the orifices 48 may serve as an interface between the fluid passages 13 and, for example, the mounting port 12 and/or the insert 18.

Figure 3:
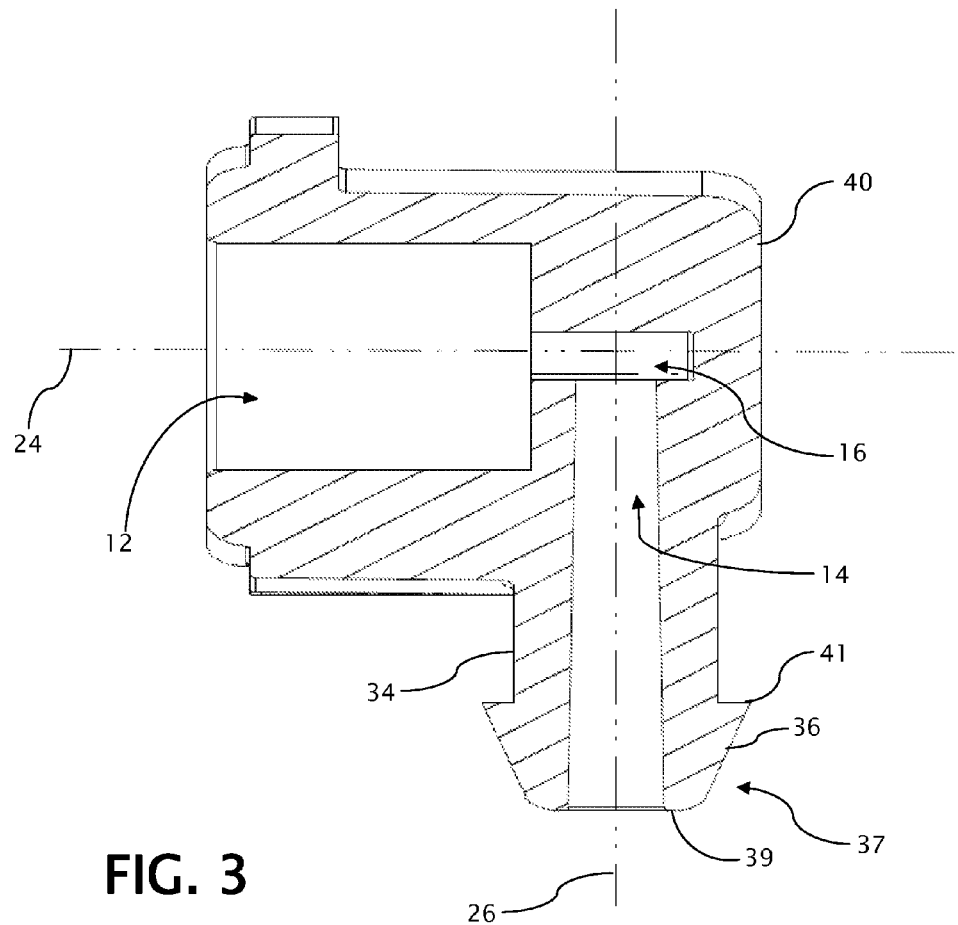
FIG. 3 is a cross-sectional view of the portion of the exemplary medical device adaptor illustrated in FIG. 2, taken along line 3-3.
Figure 4:
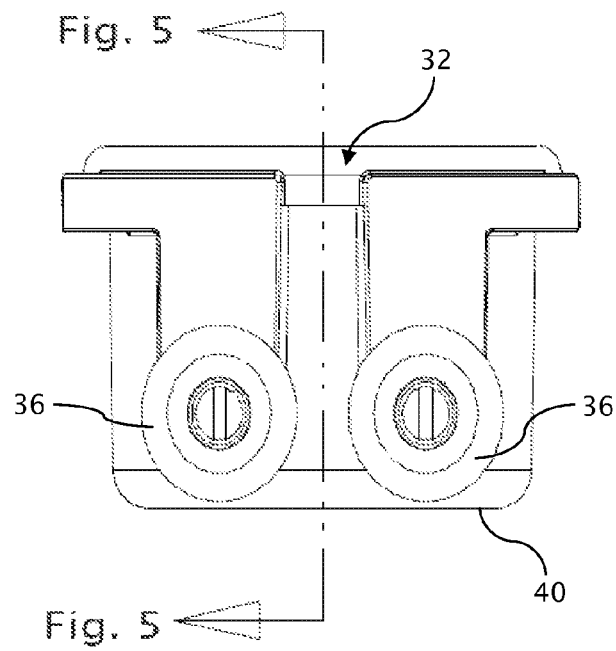
FIG. 4 is an elevation view of a portion of a medical device adaptor according to an exemplary embodiment of the present disclosure.

Each connection stem 34 may define its own individual, isolated, fluidly independent fluid passage 13. In an exemplary embodiment, at least one of the fluid passages 13 may include a first portion 14 and a second portion 16 (FIG. 3), and in additional exemplary embodiments, each of the fluid passages 13 may be formed in this way. As shown in FIG. 3, at least a portion of the first portion 14 may be formed by one of the connection stems 34, and the remainder of the first portion 14 may be formed by the housing 40. The second portion 16 may be formed by, for example, the housing 40 and/or the ceiling 44. In an exemplary embodiment, each connection stem 34 may define a longitudinal axis 26, and in such an exemplary embodiment, the first portion 14 of the fluid passage 16 may extend substantially along and/or parallel to the longitudinal axis 26 of the respective connection stem 34. In addition, the housing 40 of the adaptor 10 may define a central axis 24 extending through a central portion thereof. In such an exemplary embodiment, the second portion 16 of the fluid passage 13 may extend substantially along and/or parallel to the central axis 24. In an exemplary embodiment, the longitudinal axis 26 of the connection stem 34 may extend substantially perpendicular to the central axis 24 of the housing 40.

Although not illustrated in FIG. 3, it is understood that in additional exemplary embodiments of the present disclosure, the longitudinal axis 26 of the respective connection stems 34 may extend substantially parallel to the central axis 24 of the housing 40. In such an exemplary embodiment, the connection stems 34 may extend substantially perpendicular to, for example, the ceiling 44. In such an exemplary embodiment, the second portion 16 may merge with the first portion 14 such that the fluid passages 13 may extend substantially linearly through the connection stems 34 from the ceiling 44. Such a design may simplify the manufacture of the adaptor 10 and may be useful in known medical device applications.

The diameter, length, shape, and/or other configurations of the first portion 14 of the fluid passages 13 may be dictated by, for example, the diameter, length, and other configurations of the connection stems 34. Likewise, the length, diameter, shape, and/or other configurations of the second portion 16 of the fluid passages 13 may be limited and/or otherwise determined by the configurations of the ceiling 44 and/or housing 40. For example, the orifices 48 may be positioned at a sufficient distance from, for example, the wall 46 so as to allow for face sealing of fittings disposed within the mounting port 12 on a sealing surface 22 of the insert 18. Such face sealing may deform at least a portion of the insert 18, and the orifices 48 may be disposed at a sufficient distance from the wall 46 such that the deformation of the insert 18 does not result in blockage or partial blockage of the orifices 48 by the insert 18.

The adaptor 10 may include at least one mounting shoulder 28, and the mounting shoulders 28 may be any tab, extension, shelf, notch, groove, lip, ridge, flange, or other like structure useful in catching, latching, orienting, supporting, and/or otherwise connecting the adaptor 10 with, for example, a corresponding fitting. As shown in at least FIGS. 1 and 7, the mounting shoulders 28 may be formed by, for example, at least a portion of the housing 40. Alternatively, one or more of the mounting shoulders 28 may be formed separate from the housing 40 and may be fixedly mounted to the housing 40. In an exemplary embodiment, at least a portion of the mounting shoulders 28 may extend along the outer wall 38 of the adaptor 10, and may extend substantially laterally from and/or substantially transverse to the outer wall 38.

As illustrated in FIG. 7, in an exemplary embodiment, the mounting shoulders 28 may include a radius portion 31 and a ledge 29. The radius portion 31 may have any contour and/or other configuration useful in facilitating connection between the adaptor 10 and, for example, known medical device fittings. For example, the radius portion 31 may facilitate at least a portion of such a known fitting to slide and/or otherwise be guided along the mounting shoulder 28 while the fitting is being connected and/or otherwise mated with the adaptor 10. The radius portion 31 may be disposed proximate a bottom portion 33 of each respective mounting shoulder 28 to facilitate such connectability.

Figure 9:
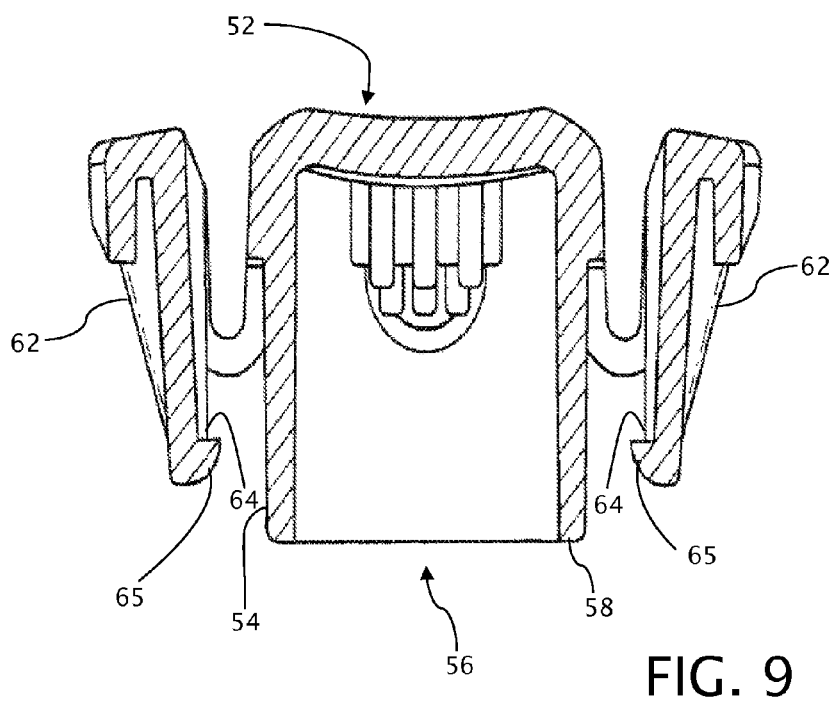
FIG. 9 is an exemplary cross-sectional view of the fitting illustrated in FIG. 8.
Figure 10:
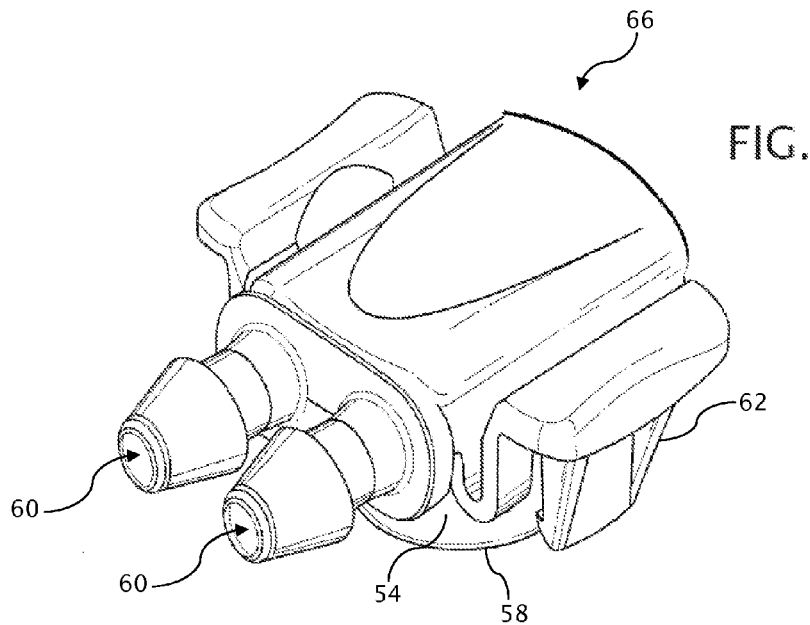
FIG. 10 is an isometric view of an additional exemplary standardized fitting.
Figure 11:
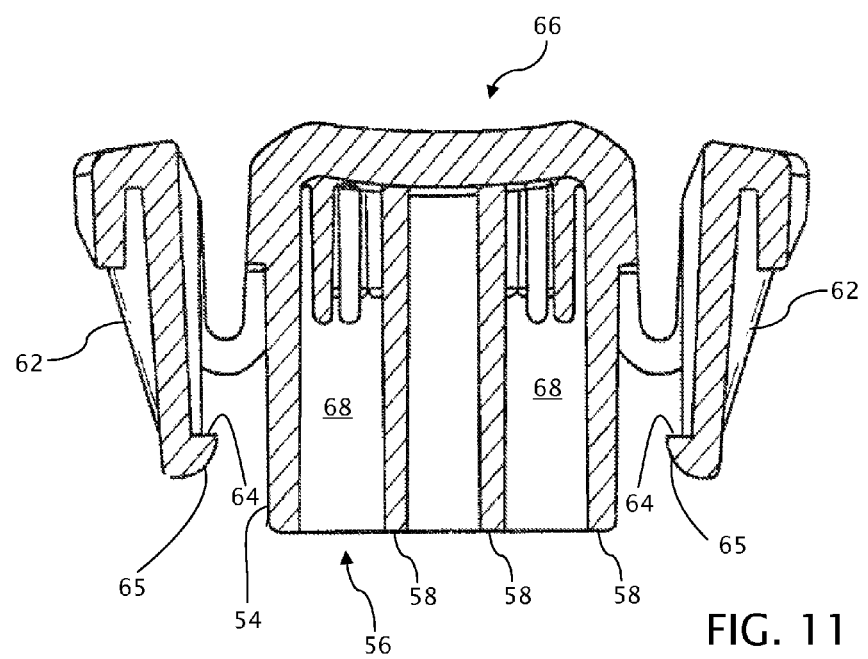
FIG. 11 is an exemplary cross-sectional view of the fitting illustrated in FIG. 10.

The ledge 29, on the other hand, may be disposed opposite the radius portion 31 adjacent to the outer wall 38. The ledge 29 may be a substantially flat shelf-like portion of the mounting shoulder 28 configured to retain a connective structure of the mated fitting. For example, with reference to the embodiments illustrated in FIGS. 8 through 11, known standardized fittings 52, 66 may include one or more attachment legs 62 configured to assist in removably attaching the fittings 52, 66 to diagnostic equipment or other like medical devices. Due to the configuration of the adaptor 10, however, these known fittings 52, 66 may be removably attachable to the adaptor 10 in situations where diagnostic equipment having connection ports that are not compatible with the fittings 52, 66 are in use. In such situations, the fittings 52, 66 may be removably attached directly to the adaptor 10, and the mounting shoulders 28 may facilitate such connection. For example, as shown in FIGS. 9 and 11, the attachment legs 62 may each define a toe 64 and a radius portion 65. In attaching the fittings 52, 66 to the adaptor 10, the radius portion 65 may mate with the radius portion 31, and these two positions may become slidably engaged until, for example, the toe 64 clears the ledge 29 of the mounting shoulder 28. Each attachment leg 62 may be springedly and/or otherwise flexibly attached to the body of the fittings 52, 66 such that when the toe 64 clears the ledge 29 of the adaptor 10, the toe 64 may snap to and/or otherwise mate with the substantially planar ledge 29, and may be retained thereby. Thus, the attachment legs 62 may releasably lock the fittings 52, 66 in place on the adaptor 10 during use.

As is also shown in FIG. 7, the mounting shoulders 28 may be exposed by and/or at least partially formed by the flange 30 disposed on the outer wall 38 of the adaptor 10. The flange 30 may extend along at least a portion of the outer circumference of the housing 40 and, as illustrated in FIGS. 1 and 7, the flange 30 may extend substantially transverse to the outer wall 38.

The flange 30 may define one or more gaps 32. The gaps 32 may comprise breaks in the flange 30, and each of the mounting shoulders 28 may be disposed within and/or otherwise defined by the gaps 32 of the flange 30. The gaps 32 may have any useful length, width, depth, and/or other dimension, and it is understood that the gaps 32 and/or the mounting shoulders 28 may assist in, among other things, orienting and/or aligning the fittings 52, 66 for connection with the adaptor 10. For example, the length, width, depth, and/or other dimensions of the gaps 32 may substantially correspond to the length, width, depth, and/or other dimensions of the respective attachment legs 62 of the fittings 52, 66 to be disposed within the gaps 32 during use. In an exemplary embodiment, the gaps 32 may be spaced and/or otherwise disposed approximately 180 degrees apart from each other along the outer circumference of the housing 40. Such spacing may substantially match the location of the corresponding attachment legs 62 on a circumference of the fittings 52, 66. Accordingly, the gaps 32 may guide the alignment and/or orientation of the fittings 52, 66 upon connection with the adaptor 10. The location and/or orientation of the gaps 32 may match that of the attachment legs 62 such that the fittings 52, 66 may only be connected to the adaptor 10 in a single desired orientation. However, in an exemplary embodiment in which the gaps 32 are spaced by 180 degrees, it is understood that the fittings 52, 66 may be connected to the adaptor 10 in two opposite directions (for example, 180 degrees apart).

The gaps 32 may assist in aligning the fittings 52, 66 with the adaptor 10 such that when connected thereto, the individual fluid passages 13 defined by the adaptor 10 may be substantially aligned with corresponding individual fluid passages defined by the fittings 52, 66. For example, in the embodiment shown in FIGS. 8 and 9 in which the fitting 52 defines a single fluid passage 60, the fluid passage 60 may be fluidly connected to each of the fluid passages 13 of the adaptor 10 when the fitting 52 is attached thereto. The fitting 52 may define an undivided orifice 56 to enable this fluid connection via, for example, the thru holes 20 of the insert 18. Alternatively, in the embodiment of FIGS. 10 and 11 in which the fitting 66 defines two individual fluid passages 60, and respective individual channels 68 fluidly connected and corresponding to each one of the fluid passages 60, each dedicated channel 68 may be fluidly connected to a single corresponding individual fluid passage 13 of the adaptor 10. Such a fluid connection may be made through, for example, respective thru holes 20 of the insert 18, and the gaps 32 may assist in orienting the fitting 66 with respect to the adaptor 10 to facilitate and assist in maintaining such substantially separate, independent, and individual fluid passages. As shown in FIG. 11, the orifice 56 of the fitting 66 may be substantially bifurcated to assist in separating the fluid passages described above.

Figure 2:
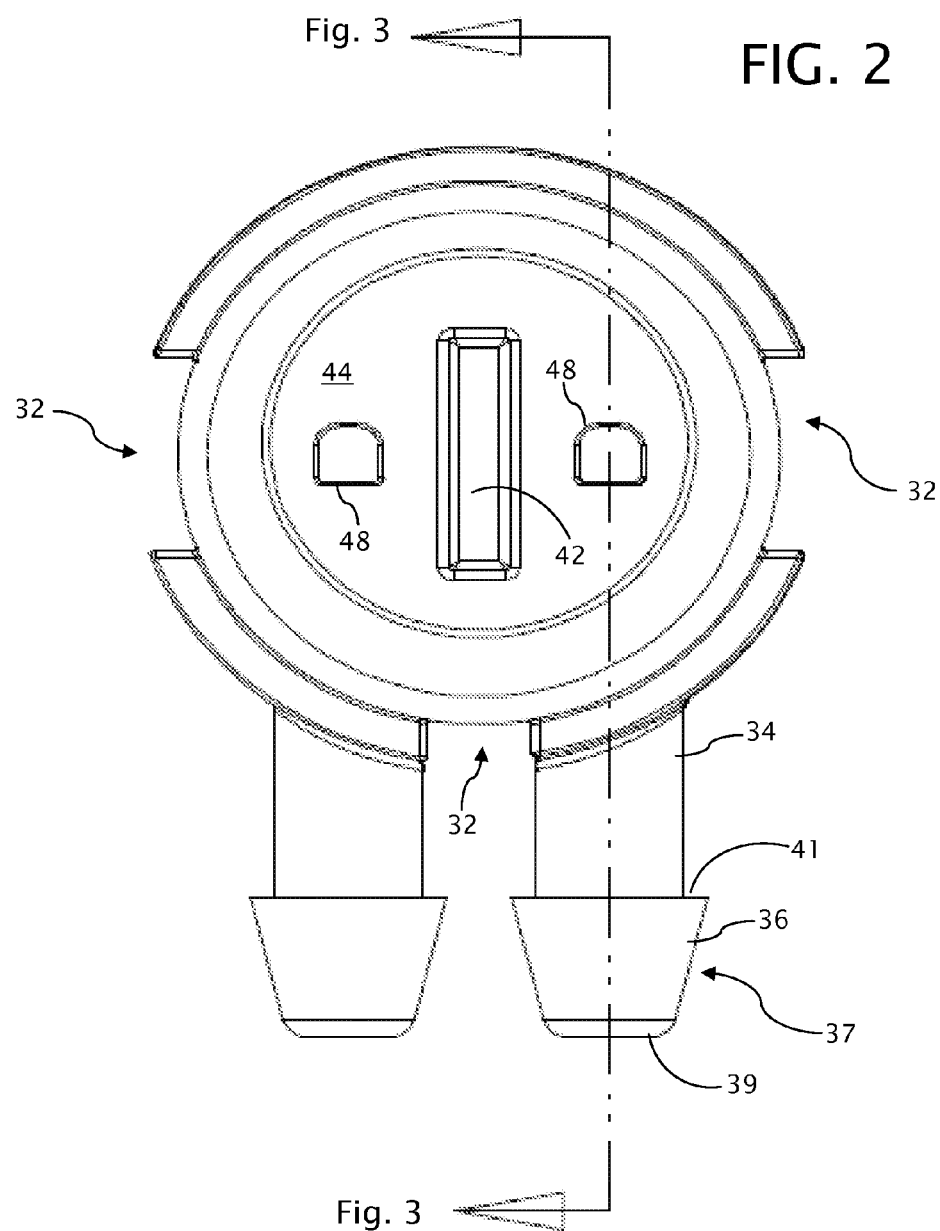
FIG. 2 is a plan view of a portion of a medical device adaptor according to an exemplary embodiment of the present disclosure.

As shown in FIG. 1, the connection stems 34 may extend transverse from the outer wall 38. The connection stems 34 may be of any shape, size, and/or other configuration to facilitate connection with any known signal carrying and/or transmitting device such as, for example, medical hoses, cannulas, surgical tubing, and the like. As shown in at least FIGS. 2 and 3, each connection stem 34 may include at least one barb 36 at a distal end 37 thereof. Although the figures of the present disclosure illustrate connection stems 34 including only a single barb 36, in additional exemplary embodiments, at least one of the connection stems 34 of the adaptor 10 may include two or more barbs 36 to assist in connecting with the signal carrying devices discussed above. The connection stems 34 may have a substantially standard length to facilitate such a connection. Moreover, the connection stem 34 and the corresponding barb 36 may have a substantially standard diameter corresponding to the inside diameter of the tubing, hoses, cannulas, and/or other signal carrying devices connected thereto.

In addition, although a tip 39 of the barb 36 may be substantially rounded and/or otherwise a-traumatic, a proximal end 41 of the barb 36 may be left substantially sharp in exemplary embodiments of the present disclosure in order to facilitate and/or otherwise assist in forming a substantially fluid-tight seal between the connection stem 34 and the inside diameter of the signal carrying device. In such an exemplary embodiment, the relatively sharp proximal end 41 of the barb 36 may dig and/or cut at least partially into the inner wall of the signal-carrying device to form such a seal.

In an exemplary embodiment, the connection stems 34 may be separated by an additional gap 32 formed by the flange 30. In an exemplary embodiment, the gap 32 may resemble a channel formed by the outer wall 38 of the adaptor 10, and such a channel may extend substantially the entire height of the outer wall 38. The gap 32 between the connection stems 34 may assist in maintaining, for example, the dimensions and/or tolerancing of the components of the adaptor 10 during a molding and/or other fabrication process. For example, in embodiments in which the adaptor 10 is formed through a molding process, the gap 32 may facilitate more stable and repeatable curing, and may assist in minimizing the distortion of, for example, the inner diameter of the mounting port 12 or the wall 46. The gap 32 separating the connection stems 34 may also assist in controlling the dimensions and/or orientation of the connection stems 34 with respect to, for example, the outer wall 38. The gap 32 between the connection stems 34 may be of a common width to assist in connecting the connection stems 34 to known dual lumen signal carrying devices such as dual lumen catheters, surgical tubing, hoses, and the like.

Figure 5:
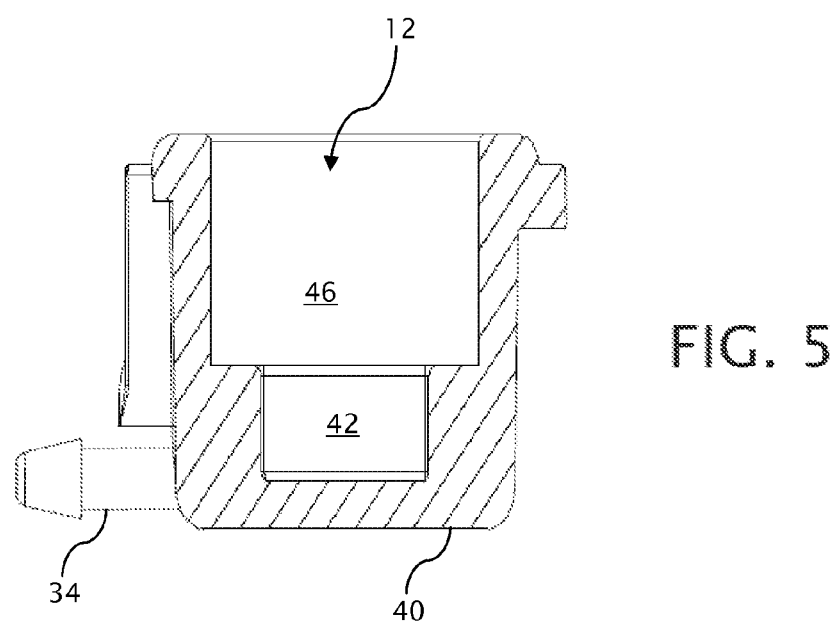
FIG. 5 is a cross-sectional view of the portion of the exemplary medical device adaptor illustrated in FIG. 4, taken along line 5-5.
Figure 8:
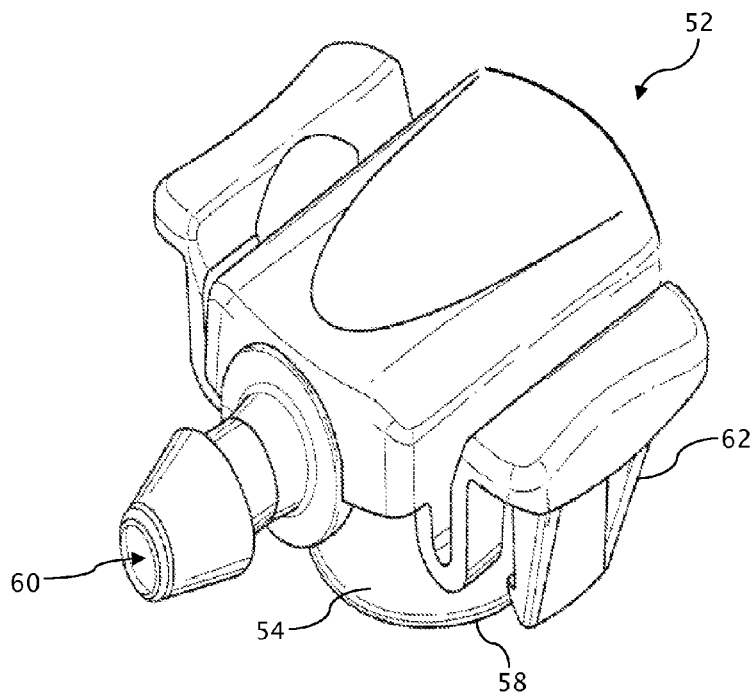
FIG. 8 is an isometric view of an exemplary standardized fitting.

The keyway 42 may be of any shape, size, and/or other configuration to assist in orienting the insert 18 with respect to the housing 40 upon insertion within the mounting port 12. For example, the keyway 42 may assist in orienting the insert 18 such that the thru holes 20 defined thereby substantially overlay the respective orifices 48 defined by the ceiling 44. Such orientation may assist in fluidly connecting the thru holes 20 to the corresponding orifices 48 and/or the respective fluid passages 13. As shown in at least FIGS. 1, 2, and 5, the keyway 42 may be substantially rectangular, substantially square, and/or any other shape. In an exemplary embodiment, the keyway 42 may be configured to substantially match the shape, size, and/or other configurations of a key 50 defined by the insert 18. Such an exemplary key 50 is illustrated in FIG. 6. The keyway 42 may be defined by, for example, the ceiling 44 and/or the wall 46 of the housing 40. An exemplary keyway 42 defined by the wall 46 may comprise a channel, grove, and/or other like configuration. The keyway 42 may be disposed between, for example, fluid passages 13 of the adaptor 10, and the keyway 42 may be sized and/or located to assist in maintaining adequate separation between the independent fluid passages 13. In an exemplary embodiment, the keyway 42 may be substantially centrally disposed within the ceiling 44 and/or the mounting port 12. In additional exemplary embodiments, the adaptor 10 may include more than one keyway 42 to facilitate orientation of the insert 18, and in such exemplary embodiments, the insert 18 may define a corresponding number of keys 50 to mate with each respective keyway 42.

In an additional exemplary embodiment, the keyway 42 may have a length and/or width that is slightly smaller than the corresponding length and/or width of the key 50 such that the key 50 may be press-fit within the keyway 42 upon connecting the insert 18 to the housing 40. In such an exemplary embodiment, the key 50 may deform slightly upon insertion into the keyway 42, and the tight tolerancing between the keyway 42 and the key 50 may assist in retaining the insert 18 within the mounting port 12 while the adaptor 10 is not in use. As discussed above, in additional embodiments, the insert 18 may be omitted, and in such an exemplary embodiment, a fitting 52, 66 or other like component mated with the adaptor 10 may form a substantially fluid-tight seal directly therewith upon connection. In such an exemplary embodiment, the ceiling 44 and/or the wall 46 may facilitate such a direct substantially fluid-tight seal.

The insert 18 may be, for example, any known gasket, elastomeric plug, O-ring, and/or other sealing structure known in the art. As shown in FIGS. 1 and 6, an exemplary insert 18 may be substantially cylindrical and/or disc-shaped, and the shape, size, and/or other configurations of the insert 18 may be selected to substantially correspond with the dimensions and/or configurations of the mounting port 12 and/or the ceiling 44. As discussed above, the key 50 may be configured to form a tightly toleranced fit with the keyway 42. In addition, the outer diameter of the insert 18 may be chosen to substantially match the inner diameter of the mounting port 12 and/or the wall 46. In an exemplary embodiment, the diameter of the insert 18 may be slightly larger than the inner diameter of the mounting port 12. In such an exemplary embodiment, the slightly larger diameter of the insert 18 may assist in forming a substantially fluid-tight seal between the insert 18 and the wall 46 of the mounting port 12 when the insert 18 is disposed therein. In addition, such a tightly toleranced fit may assist in retaining the insert 18 within the mounting port 12 while the adaptor 10 is not in use. As discussed with regard to the key 50, such a tightly toleranced fit between the wall 46 and the insert 18 may cause the insert 18 to compress and/or deform slightly upon insertion within the mounting port 12.

The insert 18 may have at least two sides, and in an exemplary embodiment, the insert 18 may define a sealing surface 22 on a first side and a mating surface 21 on an opposite side thereof. Upon connecting the insert 18 to the housing 40, the mating surface 21 may abut the ceiling 44. In addition, when the fitting 52, 66 is connected to the adaptor 10 during use, at least a portion of the fitting 52, 66 may form a substantially fluid-tight seal with the sealing surface 22. For example, as shown in FIGS. 9 and 11, the fittings 52, 66 may define a sealing face 58 disposed at the base of a stem 54. The sealing face 58 may be, for example, a perimeter of the stem 54. The stem 54 may be sized, shaped, and/or otherwise configured for insertion into the mounting port 12 upon connecting the fitting 52, 66 to the adaptor 10.

Upon releasably latching and/or otherwise connecting the attachment legs 62 to the corresponding mounting shoulders 28, the stem 54 may be pressed into the insert 18 causing at least a portion of the insert 18 to compress and/or otherwise deform. In such exemplary embodiments, the sealing face 58 may form a substantially fluid-tight seal with the sealing surface 22 of the insert 18, and the insert 18 may be compressed between the ceiling 44 and the sealing face 58. In addition, in the exemplary embodiment of FIGS. 10 and 11 in which the fitting 66 comprises two fluid passages 66 and two corresponding channels 68, each of the channels 68 may form at least a portion of the sealing face 58. Accordingly, when the fitting 66 is connected to the adaptor 10, the channels 68 may form individual substantially fluid-tight seals with the sealing surface 22. In such an exemplary embodiment, each channel 68 may be fluidly connected to a corresponding thru hole 20 of the insert 18, and the substantially fluid-tight seal discussed above may assist in maintaining the fluid passages 60 and channels 68 of the fitting 66 independent from one another.

Figure 12:
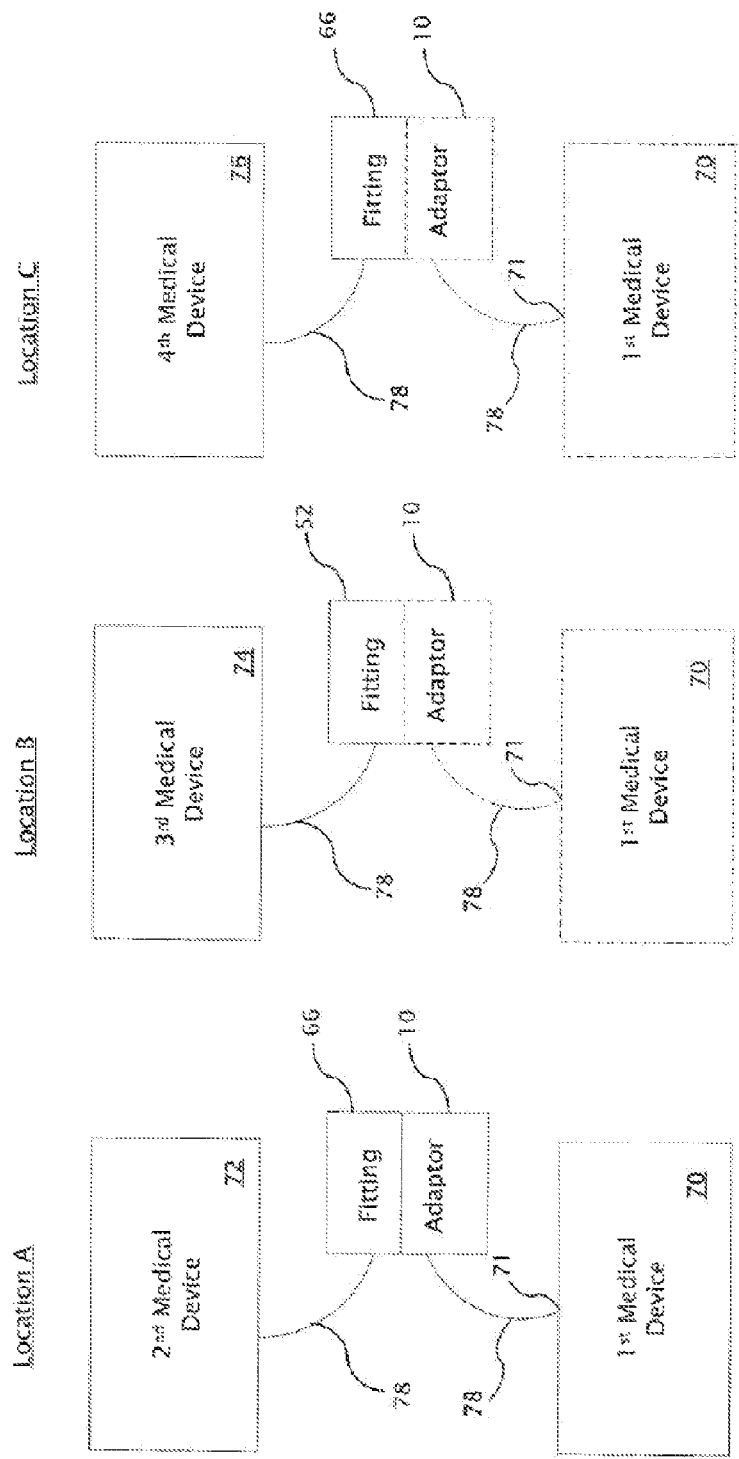
FIG. 12 is a schematic diagram illustrating the use of a medical device adaptor with multiple standardized fittings according to an exemplary embodiment of the present disclosure.

The schematic diagram shown in FIG. 12 illustrates an exemplary method of utilizing an adaptor 10 of the present disclosure. FIG. 12 is merely representative of an exemplary use of the adaptor 10, and additional uses or methods of the adaptor 10 are envisioned in the present disclosure. Accordingly, the description of FIG. 12 should not be interpreted to limit the scope of the present disclosure in any way.

As shown in FIG. 12, different Locations A, B, C in, for example, an exemplary healthcare facility may each utilize unique medical devices 72, 74, 76. Such medical devices 72, 74, 76 may be, for example, any of the blood pressure monitors, acoustic medical instruments, electrocardiographic devices, and/or other common medical gages, monitors, meters, sensors, instruments or the like. In an additional exemplary embodiment, at least one of the medical devices 72, 74, 76 may be a stethoscope and each of the medical devices 72, 74, 76 in the different Locations A, B, C may be equipped with one of the standardized fittings 52, 66 discussed above with regard to FIGS. 8-11. Moreover, the fittings 52, 66 may be fluidly and/or otherwise operably connected to the medical devices 72, 74, 76 via a single or dual lumen signal-carrying device 78 of the type described herein.

In an exemplary embodiment of FIG. 12, the fittings 52, 66 may be standardized fittings utilized throughout the healthcare facility to streamline diagnosis and treatment of the facility's patients. Such patients may be fitted with one or more medical devices such as, for example, blood pressure cuffs or other diagnostic equipment, and such devices are typically equipped with universal connectors configured to mate with standardized fittings 52, 66. In such a scenario, the adaptor 10 described in the present disclosure may not be required since the fitting 52, 66 may be directly connected to the universal connectors of such medical devices.

However, FIG. 12 is illustrative of a situation in which a patient has been fitted with a medical device 70 having a connector 71 that is not configured to mate with the standardized fitting 52, 66. In such a scenario, the adaptor 10 may be used to form a fluid connection between the standardized fitting 52, 66 and the nonconforming connector 71 of the medical device 70. Such a connection may be facilitated by one or more signal carrying devices 78 fluidly and/or otherwise operably connected between the adaptor 10 and the nonconforming connector 71. As shown in FIG. 12, the adaptor 10 may remain connected to the medical device 70 for use in each of the Locations A, B, C without requiring the removal and replacement of the medical device 70.

As described above, and in additional exemplary embodiments, at least one of the medical devices 72, 74, 76 may comprise a stethoscope or other like device, and attaching a standardized fitting 52, 66 thereto may enable the user to utilize one or more disposable components therewith. For example, it may be convenient for a healthcare professional to utilize a disposable stethoscope head to avoid cross-contamination between consecutive patients. Ordinarily, a standardized disposable stethoscope head may be connected to the standardized fittings 52, 66, and the disposable head may be disposed of after each use. However, in a situation in which a disposable stethoscope head having a nonconforming connector 71 is utilized, the connector 71 may be fluidly and/or otherwise operably connected to an adaptor 10 of the present disclosure. The adaptor 10 may be connected to the fitting 52, 66 such that the stethoscope head may still be used in connection with the standardized stethoscope 72.

On each of the exemplary embodiments described herein, the signals passed between the first medical device 70 and the downstream medical device 72, 74, 76 may be any light signal, air signal, electrical signal, sound signal, pressure signal, and/or like signal utilized in medical diagnosis and treatment. The separate individual fluid passages 13 of the adaptor 10 may be configured to minimize and/or substantially eliminate, for example, noise or other interference caused by different signals being transmitted via the respective fluid passages 13. It is understood that such signals may pass through the thru hole 20 of the insert 18 in passing between the adaptor 10 and the fitting 52, 66.

The invention has been described in detail with particular reference to exemplary embodiments, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. A medical device adaptor removably connectable to a fitting, the adaptor comprising:
    a fluid passage extending substantially through the adaptor and configured for fluid connection with the fitting;
    a mounting port, the mounting port being formed by a substantially cylindrical wall of the adaptor and a ceiling of the adaptor, the ceiling extending substantially perpendicularly from the wall;
    a mounting shoulder configured to mate with an attachment leg of the fitting extending from the wall;
    a central axis, the central axis extending substantially centrally through the ceiling;
    a keyway defined by the ceiling, the central axis passing through the keyway;
    an insert, the insert defining a thru hole to at least partially align with the fluid passage and wherein the insert defines a key for disposing within the keyway, the key to orientate the insert relative to the fluid passage; and
    wherein the insert defines a substantially planar sealing surface proximate the thru hole; and
    a sealing surface configured to form a substantially fluid-tight seal with a corresponding surface of the fitting, the sealing surface remaining substantially fixed relative to the corresponding surface of the fitting when the adaptor is removably connected to the fitting.

2. The adaptor of claim 1, wherein the fitting defines a fluid passage, the fluid passage of the fitting being fluidly connected to the fluid passage of the adaptor upon connecting the fitting to the adaptor.

3. The adaptor of claim 1, wherein the adaptor defines a plurality of individual fluid passages extending substantially therethrough and the fitting defines a corresponding plurality of individual fluid passages, each one of the individual fitting fluid passages being fluidly connected to a respective one of the individual adaptor fluid passages upon connecting the fitting to the adaptor.

4. The adaptor of claim 1, wherein the mounting shoulder orients the fitting relative to the adaptor upon connecting the fitting to the adaptor.

5. A medical device adaptor removably attachable to a fitting, comprising:
    a housing including:
        a mounting port, the mounting port defined by a ceiling and a wall extending from the ceiling,
        at least one connection stem,
        a keyway defined by the ceiling, the keyway disposed substantially centrally within the ceiling, and
        a fluid passage extending through the connection stem from an orifice in the ceiling; and
    an insert disposed adjacent to the ceiling, the insert defining a thru hole overlaying the orifice in the ceiling and wherein the insert defines a key disposed within the keyway, the key orienting the insert relative to the housing; and
    comprising a pair of mounting shoulders disposed substantially opposite each other along an outer surface of the housing; and
    wherein the insert defines a substantially planar sealing surface proximate the thru hole, the sealing surface being configured to remain substantially fixed relative to a separate fitting removably connectable to the mounting port.

6. A medical device adaptor, comprising:
    a housing defining:
        a mounting port having a ceiling and a circumscribing outer wall extending from the ceiling,
        a fluid passage extending substantially through the adaptor to the mounting port,
        a keyway disposed substantially centrally within the mounting port, and
        a pair of mounting shoulders spaced circumferentially along the outer wall, the pair of mounting shoulders extending transverse from the outer wall; and
    an insert disposed within the mounting port, the insert defining a thru hole at least partially aligned with the fluid passage and wherein the insert defines a substantially planar sealing surface proximate the thru hole; and
    wherein the insert defines a key disposed within the keyway, the key orienting the insert relative to the housing, the sealing surface being configured to remain substantially fixed relative to a separate fitting removably connectable to the mounting port.

7. The adaptor of claim 6, wherein a portion of the insert comprising the sealing surface has a greater elasticity than the housing.

8. The adaptor of claim 6, wherein the adaptor defines a central axis, a first portion of the fluid passage extending substantially transverse to the central axis and a second portion of the fluid passage extending substantially parallel to the central axis.

9. The adaptor of claim 6, wherein the housing includes
    a central axis extending substantially perpendicular to the ceiling, the central axis extending substantially centrally through the mounting port, wherein the keyway is formed by the ceiling and the central axis passes through the keyway.

10. The adaptor of claim 6, wherein the keyway includes a closed upper wall prohibiting passage of fluid through the keyway.

11. The adaptor of claim 1, further comprising a connection stem extending from the housing, at least a portion of the fluid passage extending through the connection stem.

12. The adaptor of claim 11, wherein the connection stem defines a longitudinal axis, the portion of the fluid passage extending along the longitudinal axis.

13. The adaptor of claim 12, wherein the thru hole extends substantially perpendicular to the longitudinal axis.

14. The adaptor of claim 12, wherein an additional portion of the fluid passage extends substantially perpendicular to the longitudinal axis.

15. The adaptor of claim 6, further comprising a flange extending along the outer wall, wherein at least one of the pair of mounting shoulders is disposed at a gap in the flange.

16. The adaptor of claim 15, wherein the gap comprises a first gap, the flange further defining a second gap, wherein the first and second gaps are disposed approximately 180 degrees apart.

17. The adaptor of claim 16, wherein a first mounting shoulder of the pair of mounting shoulders is disposed at the first gap and a second mounting shoulder of the pair of mounting shoulders is disposed at the second gap.

18. The adaptor of claim 17, further including first and second connection stems extending from the housing, the first and second connection stems being spaced by a third gap.

\* \* \* \* \*

UNITED STATES PATENT AND TRADEMARK OFFICE
CERTIFICATE OF CORRECTION

| | | |
|---|---|---|
| PATENT NO. | : 8,827,317 B2 | Page 1 of 1 |
| APPLICATION NO. | : 12/776019 | |
| DATED | : September 9, 2014 | |
| INVENTOR(S) | : Sean R. Karla et al. | |

It is certified that error appears in the above-identified patent and that said Letters Patent is hereby corrected as shown below:

IN THE CLAIMS:

In claim 11, column 14, line 46, "The adaptor of claim 1," should read --The adaptor of claim 6,--

Signed and Sealed this
Ninth Day of December, 2014

Michelle K. Lee
*Deputy Director of the United States Patent and Trademark Office*